US009615983B2

(12) United States Patent
Stryker et al.

(10) Patent No.: US 9,615,983 B2
(45) Date of Patent: Apr. 11, 2017

(54) MEDICAL EQUIPMENT WITH ANTIMICROBIAL COMPONENTS AND/OR SYSTEM

(71) Applicant: Stryker Corporation, Kalamazoo, MI (US)

(72) Inventors: Martin W Stryker, Kalamazoo, MI (US); Anuj K. Sidhu, Kalamazoo, MI (US); Adam Downey, Kalamazoo, MI (US); Cory P. Herbst, Shelbyville, MI (US); Michael W. Steffler, Kalamazoo, MI (US); Jeffrey L. Lewandowski, Delton, MI (US); Scott Davis, Oshtemo, MI (US); James T. Thwaites, Delton, MI (US); Jeffrey C. Shiery, East Leroy, MI (US)

(73) Assignee: Stryker Corporation, Kalamazoo, MI (US)

( * ) Notice: Subject to any disclaimer, the term of this patent is extended or adjusted under 35 U.S.C. 154(b) by 948 days.

(21) Appl. No.: 13/673,393

(22) Filed: Nov. 9, 2012

(65) Prior Publication Data

US 2013/0117936 A1    May 16, 2013

Related U.S. Application Data

(60) Provisional application No. 61/559,407, filed on Nov. 14, 2011, provisional application No. 61/576,075, filed on Dec. 15, 2011.

(51) Int. Cl.
*A61L 2/10*     (2006.01)
*A61L 2/08*     (2006.01)
(Continued)

(52) U.S. Cl.
CPC ............... *A61G 7/05* (2013.01); *A01N 25/08* (2013.01); *A01N 25/34* (2013.01); *A01N 59/20* (2013.01);
(Continued)

(58) Field of Classification Search
CPC ... A47C 21/042; A47C 21/044; A47C 21/048; A47C 31/00; A47C 31/007; A61L 2/03;
(Continued)

(56) References Cited

U.S. PATENT DOCUMENTS

| 2,681,061 A | * | 6/1954 | Modell | .................... | A61N 5/06 |
| | | | | | 250/495.1 |
| 3,600,126 A | * | 8/1971 | Hellund | .................... | A61L 2/14 |
| | | | | | 204/165 |

(Continued)

FOREIGN PATENT DOCUMENTS

CN        201469547 U      5/2010

OTHER PUBLICATIONS

Supplementary European Search Report for application serial No. 12849885.5, the European counterpart to U.S. Appl. No. 13/673,393.

(Continued)

*Primary Examiner* — Robert G Santos
(74) *Attorney, Agent, or Firm* — Warner Norcross & Judd LLP

(57) ABSTRACT

A patient support includes a patient support surface, a barrier adjacent the patient support surface, with a portion of the barrier or patient support surface including at least one material suspended therein, applied thereto, or embedded therein having an antimicrobial property, and an energy generation system directing energy to the portion or another portion of the barrier or patient support surface, the energy comprising a current, a field, heat, sound waves, or light to (Continued)

provide antimicrobial treatment to the portion or the other portion.

24 Claims, 13 Drawing Sheets

(51) Int. Cl.
  *A47C 31/00*  (2006.01)
  *A61G 7/05*  (2006.01)
  *A61L 2/232*  (2006.01)
  *A61L 2/235*  (2006.01)
  *A01N 25/08*  (2006.01)
  *A01N 59/20*  (2006.01)
  *A01N 25/34*  (2006.01)
  *A01N 61/00*  (2006.01)
  *A61L 2/03*  (2006.01)
  *A61L 2/04*  (2006.01)

(52) U.S. Cl.
  CPC ............ *A01N 61/00* (2013.01); *A47C 31/007* (2013.01); *A61L 2/10* (2013.01); *A61L 2/232* (2013.01); *A61L 2/235* (2013.01); *A61G 7/0506* (2013.01); *A61G 7/0507* (2013.01); *A61G 2203/16* (2013.01); *A61G 2203/70* (2013.01); *A61L 2/03* (2013.01); *A61L 2/04* (2013.01); *A61L 2/085* (2013.01); *A61L 2202/14* (2013.01)

(58) Field of Classification Search
  CPC ... A61L 2/04; A61L 2/08; A61L 2/10; A61L 2/085; A61L 2202/24
  USPC ............ 5/600, 421, 423, 652.1, 652.2, 905; 422/22
  See application file for complete search history.

(56) References Cited

U.S. PATENT DOCUMENTS

| | | | | |
|---|---|---|---|---|
| 4,772,795 | A * | 9/1988 | Sakurai | A61L 2/10 250/455.11 |
| 6,899,725 | B2 | 5/2005 | Lee | |
| 7,178,183 | B2 | 2/2007 | Cho | |
| 7,805,065 | B2 * | 9/2010 | Chan | F24C 7/04 219/405 |
| 7,914,611 | B2 * | 3/2011 | Vrzalik | A47C 21/044 5/652.1 |
| 8,100,061 | B2 * | 1/2012 | Hookway | A47B 23/046 108/26 |
| 8,118,920 | B2 * | 2/2012 | Vrzalik | A47C 21/044 5/652.1 |
| 8,229,291 | B2 * | 7/2012 | Chan | F24C 7/04 219/405 |
| 8,372,182 | B2 * | 2/2013 | Vrzalik | A47C 21/044 5/652.1 |
| 8,402,578 | B2 * | 3/2013 | Ko | A47C 21/048 5/421 |
| 8,455,832 | B2 * | 6/2013 | Statham | G01J 1/32 250/336.1 |
| 8,677,528 | B2 * | 3/2014 | Hookway | A47B 23/046 222/180 |
| 8,841,634 | B2 * | 9/2014 | Statham | G01J 1/32 250/461.1 |
| 9,095,633 | B1 * | 8/2015 | Dayton | A61L 2/10 |
| 2005/0160528 | A1 | 7/2005 | Clark et al. | |
| 2007/0110781 | A1 * | 5/2007 | Kotterer | A01N 25/34 424/405 |
| 2007/0261548 | A1 * | 11/2007 | Vrzalik | A47C 21/044 95/52 |
| 2007/0272398 | A1 * | 11/2007 | Chan | F24C 7/04 165/185 |
| 2009/0016930 | A1 * | 1/2009 | Gordon | A61L 2/14 422/22 |
| 2009/0307843 | A1 * | 12/2009 | Hookway | A47B 23/046 5/425 |
| 2010/0084122 | A1 * | 4/2010 | Chan | F24C 7/04 165/185 |
| 2010/0319125 | A1 | 12/2010 | Ko | |
| 2011/0168898 | A1 * | 7/2011 | Statham | G01J 1/32 250/354.1 |
| 2011/0219548 | A1 * | 9/2011 | Vrzalik | A47C 21/044 5/699 |
| 2012/0090091 | A1 * | 4/2012 | Hookway | A47B 23/046 5/425 |
| 2012/0144584 | A1 * | 6/2012 | Vrzalik | A47C 21/044 5/600 |
| 2012/0282135 | A1 * | 11/2012 | Trapani | A61L 2/10 422/3 |
| 2013/0117936 | A1 * | 5/2013 | Stryker | A61G 7/05 5/600 |
| 2013/0227787 | A1 * | 9/2013 | Herbst | A61G 7/1067 5/611 |
| 2013/0280126 | A1 * | 10/2013 | Statham | G01J 1/32 422/24 |
| 2014/0044590 | A1 * | 2/2014 | Trapani | A61L 2/10 422/3 |
| 2014/0374612 | A1 * | 12/2014 | Statham | G01J 1/32 250/372 |
| 2015/0037201 | A1 * | 2/2015 | Armour | A61B 19/38 422/3 |

OTHER PUBLICATIONS

PCT International Search Report, dated Nov. 12, 2012, for International Application No. PCT/US2012/064660.
PCT Written Opinion, dated Nov. 12, 2012, for International Application No. PCT/US2012/064660.

* cited by examiner

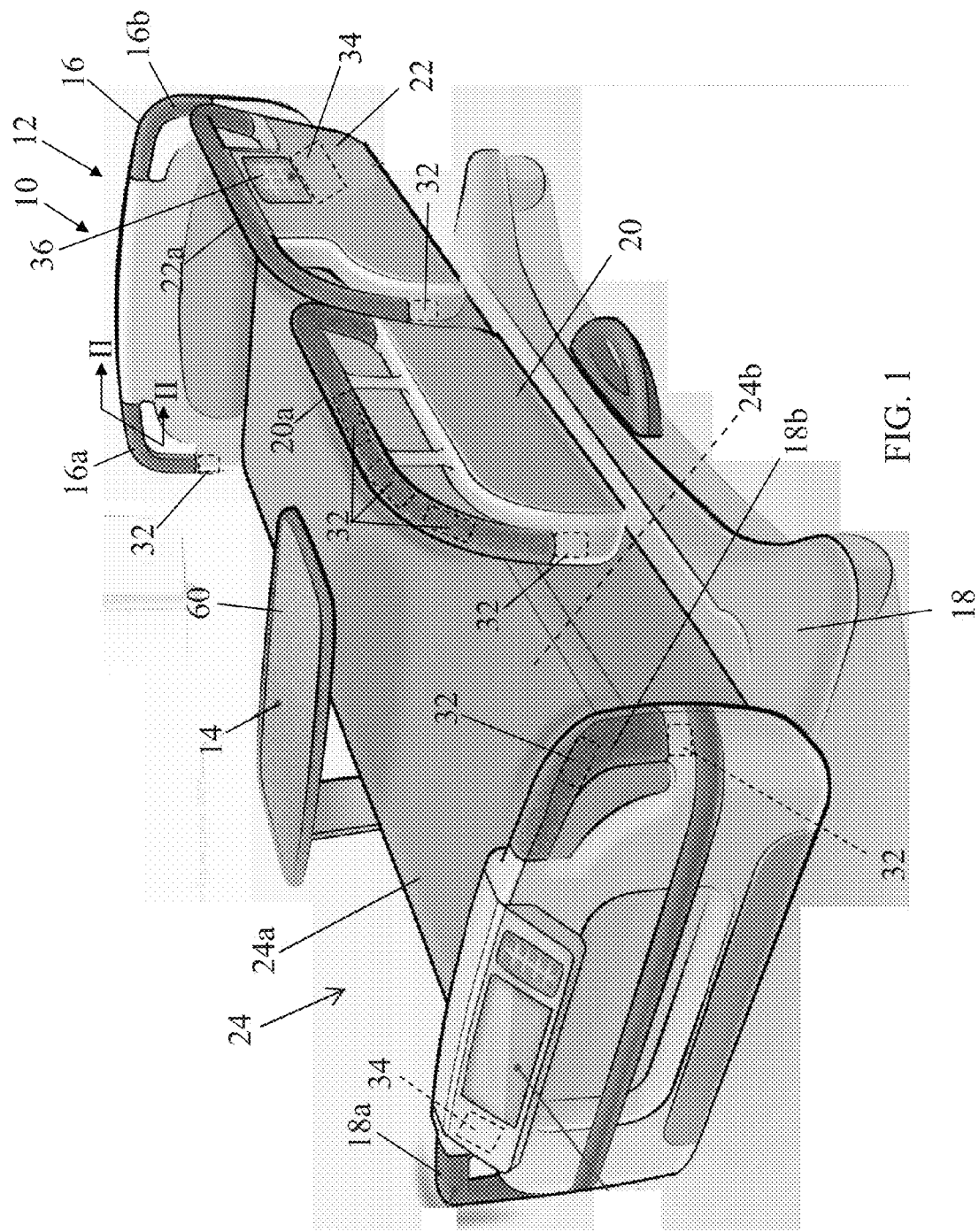

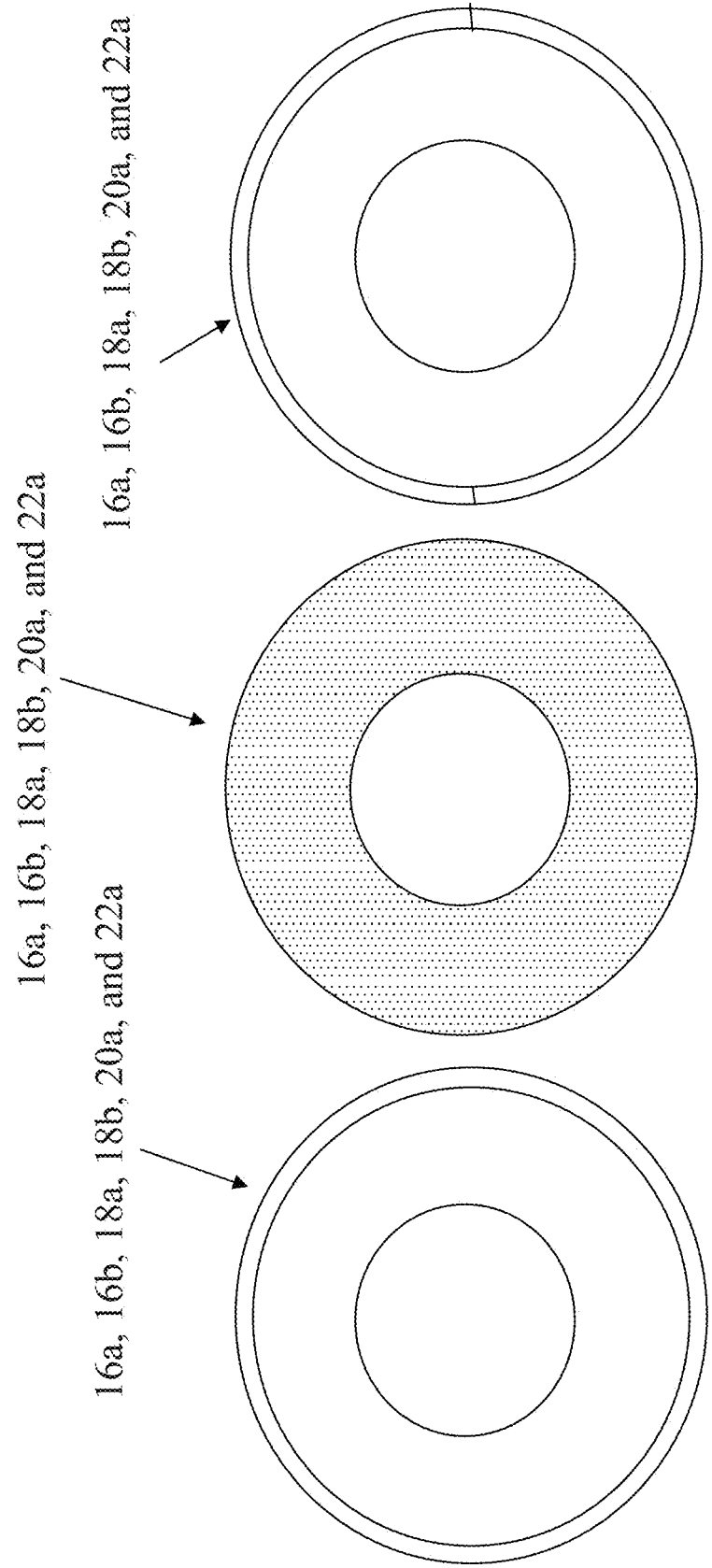

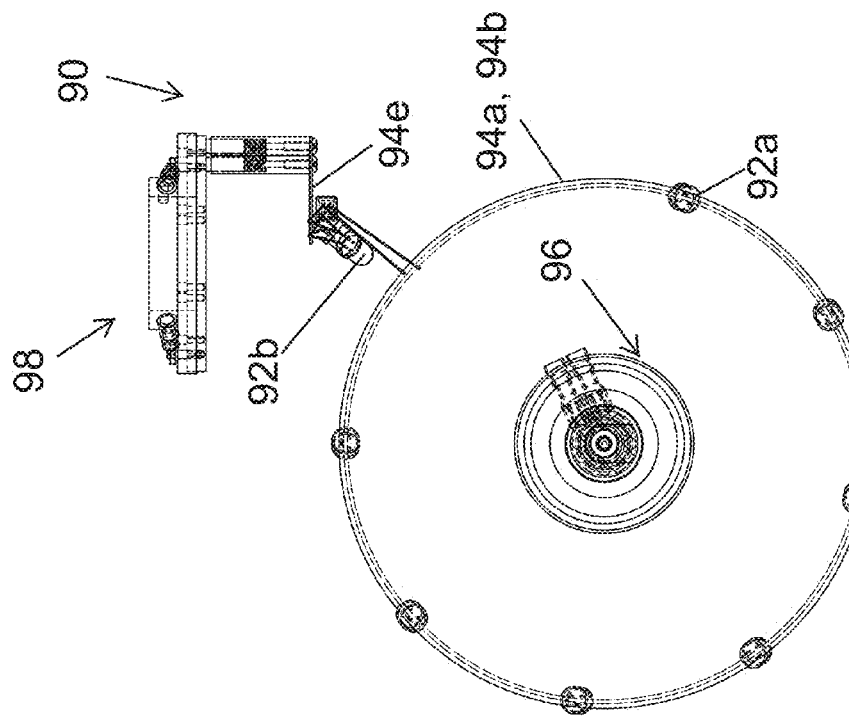
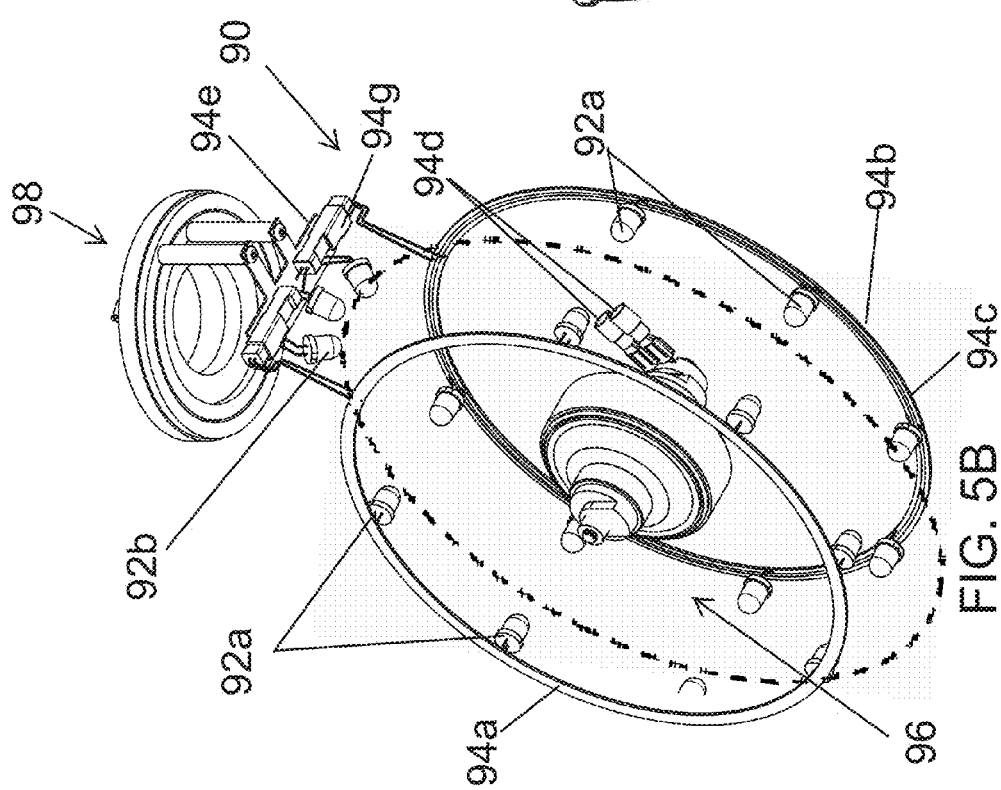

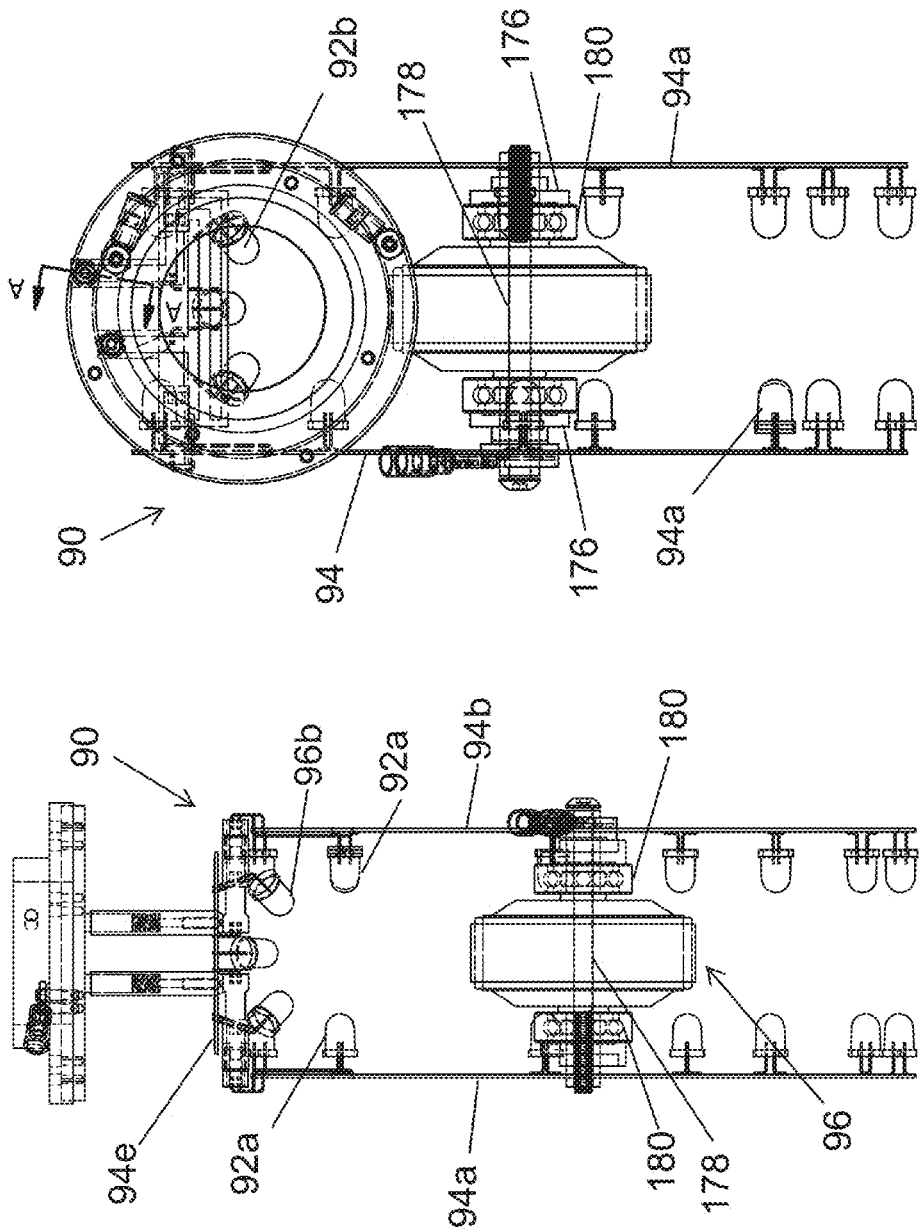

MEDICAL EQUIPMENT WITH ANTIMICROBIAL COMPONENTS AND/OR SYSTEM

The present application claims the benefit of provisional applications entitled MEDICAL EQUIPMENT WITH ANTIMICROBIAL COMPONENTS AND/OR SYSTEM, filed Nov. 14, 2011, Ser. No. 61/559,407, and MEDICAL EQUIPMENT WITH ANTIMICROBIAL COMPONENTS AND/OR SYSTEM filed Dec. 15, 2011, Ser. No. 61/576,075, which are hereby incorporated by reference herein in their entireties.

BACKGROUND OF THE INVENTION

The present invention relates to components and/or systems for controlling bacteria or reducing bacterial loads on medical equipment, including patient supports, such as beds, stretchers, cots, surgical tables, wheel chairs, furniture, and architectural components, such as a floor or wall panels, or headers, or the like.

Environmental contamination is not uncommon in hospital rooms, especially in beds and mattresses. While beds and mattresses are routinely cleaned, for example by cleaning fluids, including the chlorinated water, cleaning protocols currently used tend not to completely disinfect the respective surfaces of the bed and mattresses. Even when cleaned thoroughly, the use of chlorinated water, which destroys microorganisms on the surface, often leave the inner-most portion of the microorganism intact. Additionally, bacteria can be trapped in other particles, which can protect them against chlorination.

Consequently, alternate methods of cleaning are needed and, further, methods that will overcome the physical limitations of manual cleaning.

SUMMARY OF THE INVENTION

Accordingly, the present invention provides one or more components or a system of components that automatically clean surfaces on medical equipment, which can provide enhanced infection control.

In one form of the invention, a component of medical equipment includes a body and a material with antimicrobial properties forming, embedded in, applied to, or suspended in the body. For example, the component may comprise a side rail, a caster wheel assembly, a headboard, a foot board, or a work surface.

In one aspect where the component comprises a caster wheel assembly with a wheel, the wheel may be formed with a base material and the material with antimicrobial properties (antimicrobial material) dispersed through at least an outer layer of the base material. Further, the base material is selected so that that overtime it wears down so that the antimicrobial material dispersed beneath the outermost surface in the base material is then exposed to the ambient atmosphere to refresh the antimicrobial characteristic of the wheel.

Optionally, the equipment may also include an energy generation system to direct energy to the body to augment the antimicrobial properties of the body.

In another form of the invention, a component of medical equipment includes a body and an energy generation system for directing energy to the body to provide antimicrobial treatment to the body.

In one aspect, the component may comprise a side rail, a caster wheel assembly, a headboard, a foot board, or a work surface. For example, where the component comprises a caster wheel assembly, the energy generation system may include one or more light sources, such as a UV light source, including a UV-C light source, for directing energy to the wheel.

In another form of the invention, a component of medical equipment includes a body and a material with antimicrobial properties embedded in, applied to, or suspended in the body. In addition, an energy generation system directs energy to the body to augment the antimicrobial properties of the body. For example, the component may comprise a side rail, a wheel, a headboard, a foot board, or a work surface.

In one aspect, the component comprises a wheel. For example, the wheel may be formed with a material having antimicrobial properties, and the energy generation system may include one or more light sources, such as a UV light source, including a UV-C light source, for directing energy to the wheel.

In a further aspect, the wheel is at least partially covered by a shroud, with the light sources or sources housed in the shroud.

In another aspect, the medical equipment includes a power supply, and the energy generation system is powered by the medical equipment power supply. In an additional or alternate aspect, the component has a component-based power supply for powering the energy generation system. For example, in the case of a wheel, the wheel may include a hub and a hub-based dynamo for powering the energy generation system.

In another form of the invention, a patient support includes a patient support surface, a barrier adjacent the patient support surface, and at least a portion of the barrier or surface including at least one material suspended therein, applied thereto, or embedded therein having an antimicrobial property. In addition, the support includes an energy generation system that directs energy to the portion of the barrier. The energy generation system may generate a field, heat, electrical current, sound waves, or light to provide antimicrobial treatment to the portion of the barrier.

In any of the above, the antimicrobial material may comprise silver, copper or a silver or copper alloy, including copper or silver powder or a copper or silver alloy powder. Alternately, the material may comprise a silver (or silver alloy) or copper (or copper alloy) coating. Further, the material may comprise a silver (or silver alloy) or copper (or copper alloy) bodies suspended in the portion of the barrier, the surface, the body, or in a portion applied thereto. In another aspect, the material comprises a silver (or silver alloy) or copper (or copper alloy) plate.

According to yet another aspect, the energy generating systems may generate UV light or infrared light.

In yet another embodiment, the energy generating systems may generate an electric field or a magnetic field or heat.

In yet another form of the invention, a method of cleaning a surface on medical equipment includes providing a body having at least a surface with antimicrobial properties and directing energy into, onto or through the body to provide antimicrobial treatment at the surface.

In one aspect, the antimicrobial material includes coating, embedding, or dispersing antimicrobial material onto or in the body.

In another aspect, directing energy includes directing light, such as UV light, through the body. In yet another aspect, the surface is formed from a material that exhibits total internal reflectance when the light is directed into an end or a side or edge of the body such that substantially all of the light is internally reflected.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

BRIEF DESCRIPTION OF THE DRAWINGS

FIG. 1 is a perspective view of a piece of medical equipment in the form of a patient's port, namely a hospital bed incorporating the infection control system of the present invention;

FIG. 2 is a cross-section taken along line II-II of FIG. 1 illustrating one embodiment of one component of the infection control system of the present invention;

FIG. 2A is a similar view to FIG. 2 illustrating another embodiment of the infection control system of the present invention;

FIG. 2B is a similar view to FIG. 2 illustrating a third embodiment of a passive component of the infection control system of the present invention;

FIG. 5B is similar view to FIG. 5A with the wheel and bracket and part of the swivel connection removed;

FIG. 6D is the opposed side view of the wheel of FIG. 6C with the wheel removed;

FIG. 7 is a front elevation view of the active component of FIG. 5;

FIG. 8 is a top plan view of the active component of FIG. 5;

DESCRIPTION OF THE PREFERRED EMBODIMENTS

Figure 1A:
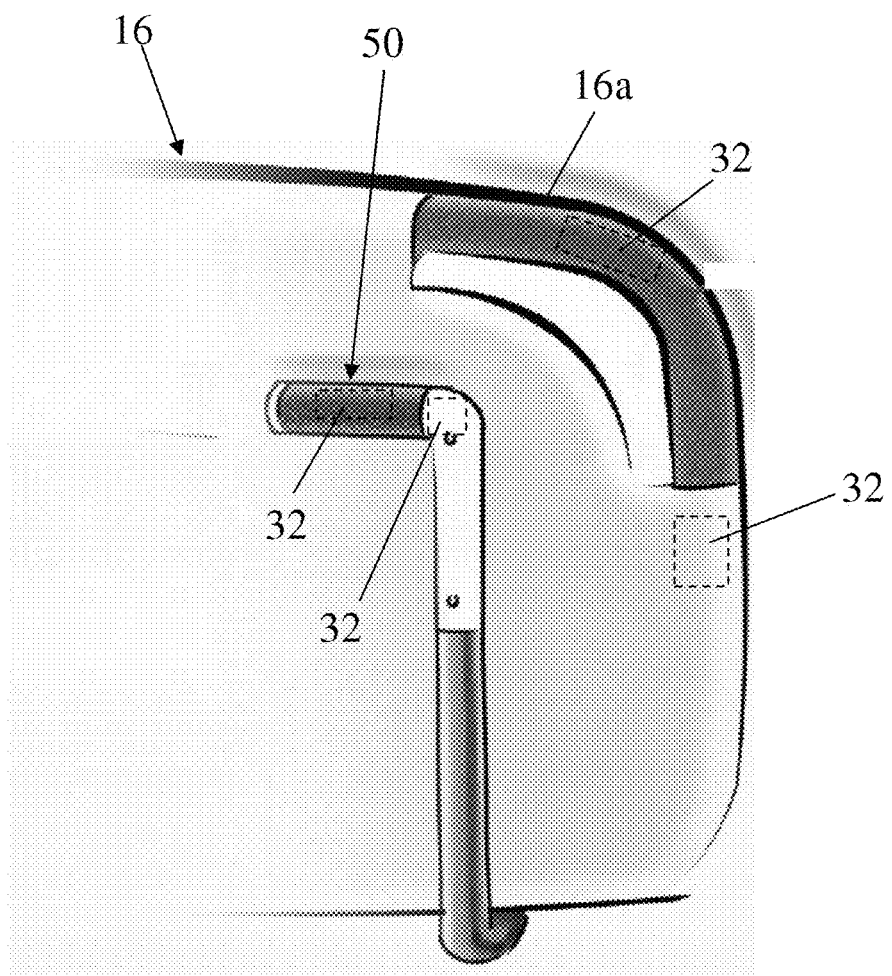
FIG. 1A is an enlarged head end view of the headboard of the bed of FIG. 1.

Referring to FIG. 1, the numeral 10 generally designates medical equipment of the present invention. In the illustrated embodiment, medical equipment 10 is in the form of a hospital bed 12 or an over-bed table 14. While the following description is made in reference to the hospital bed and over-bed table, it should be understood that the term "medical equipment" is used herein broadly and includes other types of medical equipment, such as surgical tables, wheelchairs, stretchers, cots, other hospital room furniture, including recliners, side tables, as well as structural or architectural components in a medical or hospital environment, such as headers, wall or floor panels. As will be more fully described below, one or more components of medical equipment 10 are adapted to self-clean at least over portions of their outer surfaces, especially at portions where physical contact with a patient, caregiver, or visitor is likely.

Hospital bed 12 includes a number of portions that are highly likely to be contact or touch points. Referring to FIG. 2, for example, bed 12 includes a headboard 16, a footboard 18, and side rails 20 and 22, which form a barrier around the patient support surface or mattress 24, which are commonly touched by the patient, caregiver, and/or visitors. Further, each of the headboard, footboard, and side rails have portions with greater probability of being touched, for example, handholds 16a, 16b, 18a, 18b, 20a, and 22a, which are often grabbed to maneuver or move the bed or raise or lower the side rails.

In one preferred embodiment, each of the handholds 16a, 16b, 18a, 18b, 20a, and 22a are adapted to at least reduce their bacterial load to thereby reduce the rate or chance of bacterial transmission, which could thereby improve reduce infections.

In other embodiments, a reduced group of the handholds is adapted to at least reduce their bacterial loads. While described in reference to only portions of each component of medical apparatus 10 being adapted to reduce its bacterial load, it should be understood that the entire component, e.g. the whole side rail, footboard, headboard, may be adapted to reduce its bacterial load and may incorporate one or more of the infection control system components described below.

Referring again to FIG. 2, each portion 16a, 16b, 18a, 18b, 20a, and 22a may incorporate a passive and/or an active antimicrobial component. As best seen in FIG. 2, each portion 16a, 16b, 18a, 18b, 20a, and 22a may incorporate a passive antimicrobial component, such as a coating or film or sheet formed from a material that exhibits antimicrobial characteristics. The term passive is simply used to indicate that the antimicrobial characteristics are inherent (though the ingredient having the antimicrobial characteristics may be considered to be an "active ingredient") and do not require input from another source, such as electricity, to function. For example, in one form, the material may comprise a copper or copper alloy material. Alternately, other known antimicrobial compounds or materials maybe used, such as silver or the like. The copper (or copper alloy) coating, film, or sheet optionally surrounds the entire circumference of the handhold of each barrier component or may extend only around a portion of the outer circumference of the handhold with the remaining portion optionally protected, to at least some degree, by the zone of inhibition (e.g. "halo" effect). The zone of inhibition is where the antimicrobial properties extend to the area(s) surrounding the copper.

The coating or film may be applied to the handhold by dipping, spraying or overmolding. In the case of the sheet, the sheet may be either mechanically attached or molded therein during the molding process of the handhold. When molded therein, the sheet may be molded so that it forms part of the outer surface of the handhold or may be molded so that it is slightly beneath the outer surface, where the antimicrobial properties of the sheet will still provide protection at the outer surface due to the zone of inhibition ("halo" effect).

In this manner, when a patient, caregiver, or visitor touches the handholds (16a . . . 22a) of the bed, any bacterial present on their hands if deposited on the handhold portion will, after a period of time (typically in less than 2 hours), be killed by the copper.

In another embodiment, as shown in FIG. 2A, the antimicrobial material can be dispersed, either uniformly or with different densities, throughout the material forming the handhold or may be dispersed through the outer surface of the handholds, for example, to a depth in a range of 1 mm to 10 mm or in a range of 1 mm to 5 mm or in a range of 1 mm to 2 mm. For example, the density may vary from 10% (by weight) to 80% (by weight). For example, copper (or copper alloy) may be provided in the form of powder or other particulate forms, which may be mixed with and molded with the material forming the handholds. For example, the molding method may include centrifugal molding so that the copper particles concentrate at the outer surface. After molding, and the part (e.g. handhold) is allowed to cool, the surface of the part may then be roughened, such as by sanding, to expose more of the copper. Similarly, after use of the handholds, repeated sandings or external abrasion treatments may be provided to "refresh" the surface with more copper particles. For example, the material forming the body of the hand holds may be formed from a material that with normal use wears down the outer surface sufficiently to expose more of the copper.

Referring to FIG. 2B, discrete bodies of the antimicrobial material may alternately or additionally be applied to or incorporated into the handholds, for example in the form of strips, including fibers or wires (e.g. strands), which also may be formed in the handholds during the molding process or may be "potted" into the surface using an adhesive. The spacing of the antimicrobial material bodies may be such that the zone of inhibition ("halo" effect) of each body overlaps or closely abuts the zone of inhibition ("halo" effect) of each adjacent body, though it should be understood that the bodies may be spaced further apart, especially when the antimicrobial material components are combined with other antimicrobial components or systems described more fully below.

Referring again to FIG. 1, in addition to incorporating material (or materials) with antimicrobial characteristics, bed 12 may also incorporate one or more active antimicrobial components, such as provided by antimicrobial system 30 to enhance, augment, and/or supplement the passive antimicrobial components. For example, antimicrobial system 30 may include one or more energy generators 32, which generate energy directed to or to impinge the outer surface, for example, of the handholds. Depending on the type of energy, it has been found that bacteria is either killed by certain applied energy or its DNA is affected such that it can no longer reproduce.

In one embodiment, energy generators 32 comprise UV lights, including UVC lights, such as UV LED's. UV lights have been found to disrupt bacteria's DNA and, therefore, inhibit the bacteria from reproducing. In the illustrated embodiment, the UV light is directed into the component of the bed which contains the surface on which bacteria might collect at an angle greater than the critical angle of the material forming the component so that the UV light will exhibit total internal reflection. For example, the light may be located in the barrier at an end or an edge (which can be the distal edge or an internal edge formed by an opening in the component) of the component, which may be formed from a polymer or quartz material, so that total internal reflection causes the UV light to reflect internally within the component and be guided from one end or edge to the other end or edge, which is embedded for example in the barrier. Thus, the UV light is not emitted through exterior surface of the component (or the barrier), and instead is contained within the barrier to protect a patient, caregiver, or visitors from the UV light. Therefore, when bacteria sits on the surface of the component, the component is exposed to the UV light, which as noted above interferes with the DNA of the bacteria and prevents the bacteria from reproducing.

It should be understood that two or more lights may be used, and positioned for example at the opposed ends of the component or opposed edges of the component, or at intermediate locations along the length of the component. In the latter case, the light is typically extended into an opening formed in the component and covered so that all the light enters the component, and then is internally reflected to the opposed edges or ends.

In the illustrated embodiment, energy generator 32 is located adjacent handholds 16a, 16b, 18a, 18b, 20, and 22a, which are formed from the polymer or quartz material as noted above. By positioning the UV light at one end of the handhold, light is directed from one end of the handhold to the other end, guided through the handhold by the internal reflections, much in the same manner as fiber optics. When combined with the antimicrobial properties of the antimicrobial material, such as copper, it is believed that system 30 will provide an enhanced infection control for bed 12.

In addition, system 30 may also include UV lights 34 for directing UV light into or over panels of the bed. For example, UV lights may be provided in the barrier adjacent touch screen panel 36, which may also be formed from a polymer, quartz, or glass material or have an overlay that is formed from a polymer, quartz, or glass material where total internal reflection prevents the UV light from being emitted from the exterior or outwardly facing surface of the panel and instead is guided from one edge of the panel (or overlay) to the second edge of the panel (or overlay). In this manner, bacteria that is present on the touch screen will be exposed to the UV light and thereby rendered incapable of reproducing.

Figure 3:
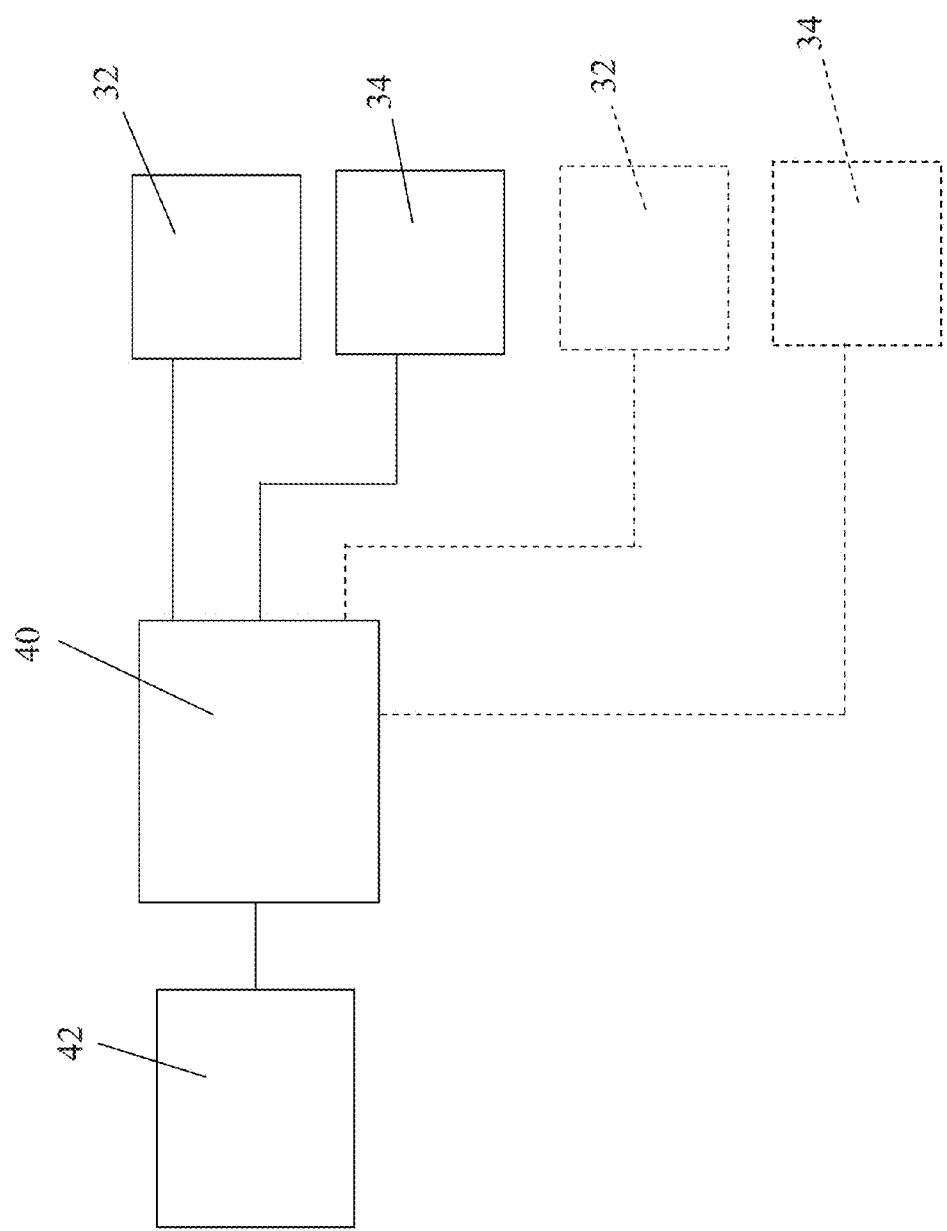
FIG. 3 is a schematic drawing of a control circuit for controlling one or more of the active components of the infection control system of the present invention.

Referring to FIG. 3, energy generator 32 and UV lights 34 may be controlled by a controller 40, which may or may not comprise the bed-based network (which controls most, if not all, the functions at the bed) and further may be remote from the bed, which is either electrically coupled to the energy generator(s) and/or lights or wirelessly coupled. For example, the controller may be a mattress-based controller, and may be incorporated into the mattress (referred to in the industry as the "surface") for example at the foot end of the mattress in a recessed formed in the underside of the mattress, such as described in U.S. Pat. Nos. 5,325,551 and 5,542,136, which are commonly owned by Stryker Corporation of Kalamazoo, Mich., and which are incorporated by reference herein in their entireties.

Controller 40 may be in communication with a user input 42, such as a touch screen or a remote control input device, to allow a user to turn on or off system 30 or allow a user to initiate a preselected activation protocol, for example, stored in controller 40. Further, system 30 may have a lock-out function that can only be unlocked by a key or code to insure that the cleaning system is only used, for example, when the bed is unoccupied. Depending on the type of energy delivered by the energy generators, system 30 may be suitable for use even if occupied.

For example, controller 40 may include appropriate software containing an activation protocol or several activation protocols and further may document when and how long the cleaning process was activated. Optionally, activation may be initiated by input from the bed. For example, the bed exit system may trigger an initiation of a cleaning cycle when the bed is exited or when the bed is designated as "not occupied". Alternately, depending on the type of energy delivered by the energy generators, the system can power the energy generator and/or UV lights continuously.

In addition to or instead of the internal lights described above, system 30 may include lights external to the bed. For example, one or more UV lights may be mounted to a wall or ceiling to direct light onto the bed so that all the external surfaces of the bed are washed with UV light. The external lights may be powered by the room power supply and also may be controlled by controller 40, for example, using RF signals, with the external lights having built therein or associated therewith a receiver and appropriate controls to power on and off the lights based on the signals from controller 40.

In another embodiment, energy generator 32 comprises a magnetic field generator that generates a magnetic field around a portion of the bed, for example the handholds. It has been found that a magnetic field can decrease formation of bacterial colony units. Optionally, the magnetic field generator may be located at several locations within each component of the barrier to wash the exterior surface of the barrier with one or more magnetic fields. Further, to minimize interference with the communication at the bed or between the bed and a device external to the bed, the magnetic field generators are sized so that their magnetic fields are localized and, further, have a strength in a range of 0.5 mT to 10 mT and moreover sufficiently attenuated to avoid any interference. The magnetic field generators may include electromagnets and/or a coil (or coils) of wire, such as copper wire, which generates a magnetic field when electricity is passed through the coil.

In yet another embodiment, energy generator 32 may comprise an electric charge generator. Again, the electric charge generator may be incorporated into the barrier component, which will generate an electric charge in the desired target, such as the handholds. The electric charge generator optionally generates an AC pulsed electrical current, which can be passed through the components, such as the handholds, which are adapted to be conductive, to kill bacteria on the handholds. For example, the handholds may be formed from plastic impregnated with carbon so that the handholds will allow low level currents to run through the handholds. Alternately or in addition, in the case of the copper wiring or fibers being embedded into the handholds, a low voltage may be applied to the copper wiring or fibers in the handholds to generate a low amperage current flow in the wires or fibers, which can generate an electric charge in the handholds. If the amperage is sufficiently low (for example, less than 10 mA if a direct current is used or less than 1 mA if an AC current is used), this charge may also be used even when the bed is occupied.

According to a fourth embodiment, energy generator 32 may comprise an acoustic generator that generates ultrasonic waves. Again as shown, the generator may be located in one or more of the various barrier components and further in close proximity to the handholds to thereby reduce the bacterial load on the handholds. The acoustic generator(s) may be located elsewhere in the bed, for example on the deck, in the mattress, or even in the base. As would be understood, the ultrasonic waves may wash the whole bed or just a portion of the bed. Similar to the other energy generators, ultrasound waves also kill bacteria, with the higher power ultrasound being especially effective over short periods of time where there are low volumes of bacteria.

In a fifth embodiment, energy generator(s) 32 may comprise one or more a heaters. For example, a suitable heater may comprise a ceramic heater or simply comprise a resistive element in a circuit, which heats up when current passes through the circuit. Alternately, the heater may comprise an infrared light (or lights), such as one or more infrared LEDs, which directs light into or onto the surface to be treated. The heaters are optionally located inside the component being thermally treated and, further, near the outer surface of the plastic or polymer skin forming the barrier so that the outer surface of the barrier will be heated to an elevated temperature that will kill the bacteria at the exterior surface of the barrier. For example, the heater or heaters are configured to generate sufficient heat so that the outer surface of the barrier is at least 50° C., at least 60° C., at least 65° C., and, further, optionally in a range of 70° C. to 100° C. In this manner, bacteria will be killed after several hours of heat application. Again, this treatment can be applied before the bed is occupied, though at lower temperatures, the heat treatment may be applied even while the bed is occupied. Because the outer surface of the barrier is formed from material having a lower heat transfer rate than, for example metal, a person can touch the barrier despite the elevated temperature without being injured. As will be understood, the higher the heat the faster the bacteria will be killed. However, to allow the heat treatment protocol to be used when the bed is occupied, it may be preferable to maintain the temperature of the exterior surface of the barrier at or below 80° C., at or below 75° C., or at or below 65° C.

In addition to handholds 16a, 16b, 18a, 18b, 20a, and 22a, it should be understood that any one or more of the described passive or active antimicrobial components may be incorporated into other components of the bed and/or, further, may be expanded to cover the entire component or barrier. For example, referring to FIG. 1A, any one or more of the described passive or active antimicrobial components may be incorporated into the handle 50 at the head end of the bed. Handles 50 may be provided on the bed to allow the bed to be moved or maneuvered, using for example a powered wheel, such as described in U.S. Pat. Nos. 6,772,850 and 7,007,765, which are incorporated by reference herein in their entireties. For example, the hand grip 62 of handle 50 may be modified or formed in the same manner as described above in reference to the handholds to thereby incorporate antimicrobial properties into the hand grips of the handles and thereby clean the hand grips.

Referring again to FIG. 1, any one or more of the passive or active antimicrobial components may be incorporated into over-bed table 14. Similar to the handholds described above, table 14 may include a table element 60, which is formed with or has applied thereto one or more copper (or copper alloy) elements (bodies, plates, fibers, powder, etc.). As an adjunct to the antimicrobial material, as described above, table 14 may also incorporate energy generating system 30 to create a synergistic reduction in the bacterial load present on the table.

Additionally, referring again to FIG. 1, any one or more of the passive or active antimicrobial components may be incorporated into mattress 24, for example, either into the cover 24a or supporting components 24b, such as the foam, gel, bladders or a combination thereof depending on the configuration of the mattress. For example, cover 24a may formed from a scrim layer (woven material) with a vinyl coating, with either the scrim layer or vinyl coating having copper, such as copper powder or copper strands or threads, incorporated therein or applied thereto. For example, the vinyl may be formed with copper powder suspended in the vinyl, which when applied to the scrim to form the cover will impart to the cover an antimicrobial characteristic.

In the case of foam or gel supporting components 24b, the passive antimicrobial components again may comprise copper bodies or particles, such as copper powder, dispersed either through a portion of the foam or gel or just in the outer regions of the foam or gel nearer the outer surface of the foam or gel. The copper may be added during the molding or forming process or may be applied post forming, such as by spraying, dipping, or the like a solution or coating with the copper suspended therein, which will adhere to and in some cases impregnate the foam or gel. In the case of bladders, the copper may be infused into the material forming the bladders or may be applied post forming, such as by spraying, dipping or the like a solution or coating with the copper suspended therein, which will adhere to and in some cases impregnate the material forming the bladders.

Thus, these applications may rely on the zone of inhibition ("halo" effect) to generate their antimicrobial effect. In addition, one or more of the active antimicrobial components may be incorporated into mattress 24. For example, the active antimicrobial component may comprise an energy generation system that generates a field, heat, electrical current, sound waves, or light, as described above, into the mattress 24 to provide antimicrobial treatment to at least a portion of the mattress. The active antimicrobial components may be incorporated into the mattress or may be incorporated into the deck or barrier of the patient support but then arranged to direct the energy to the mattress.

While described in the context of the barriers and more specifically the handholds of the barrier components, as noted other components of the bed may also incorporate one or more passive or active antimicrobial components described above. For example, the mattress, the deck, or any or all of the buttons that activate various features of the bed may also incorporate one or more passive and/or active antimicrobial components.

Figure 4:
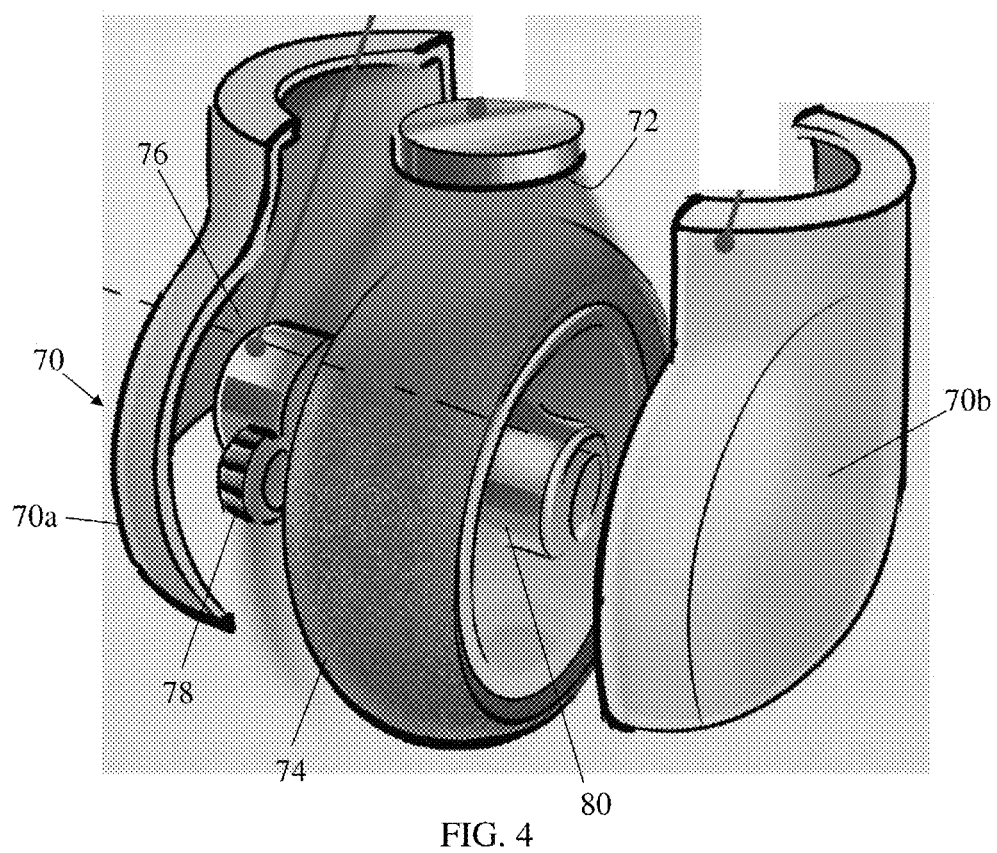
FIG. 4 is an exploded perspective view of a castor wheel assembly of the bed of FIG. 1.
Figure 5:
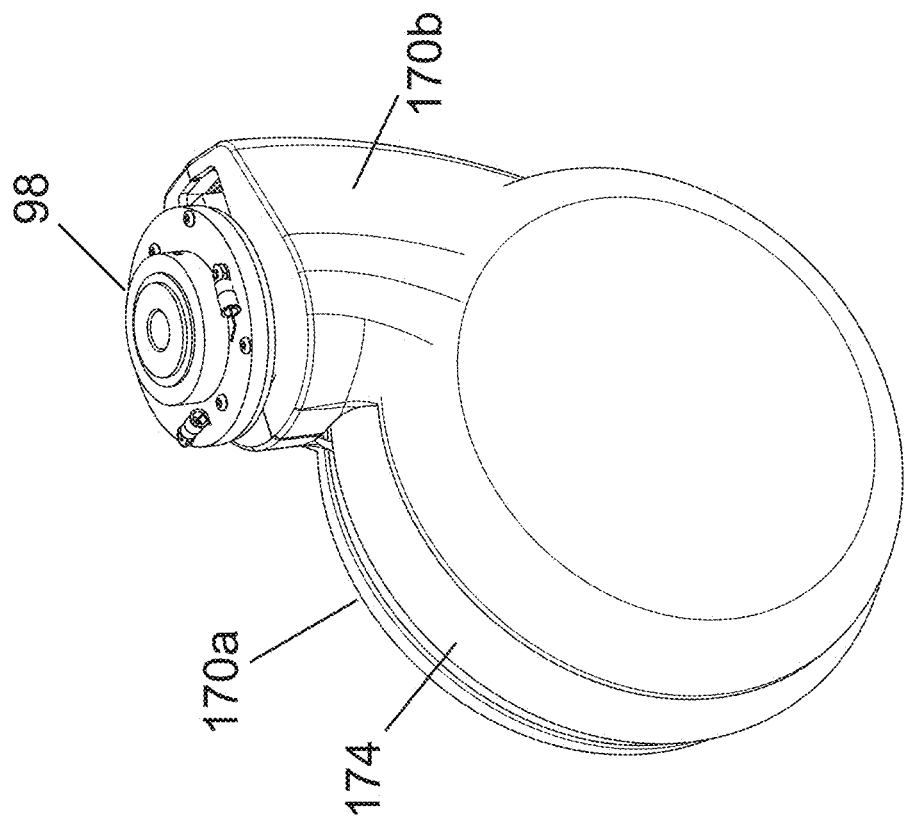
FIG. 5 is a perspective view of one embodiment of the active component of a castor wheel assembly suitable for use on the bed of FIG. 1.
Figure 6:
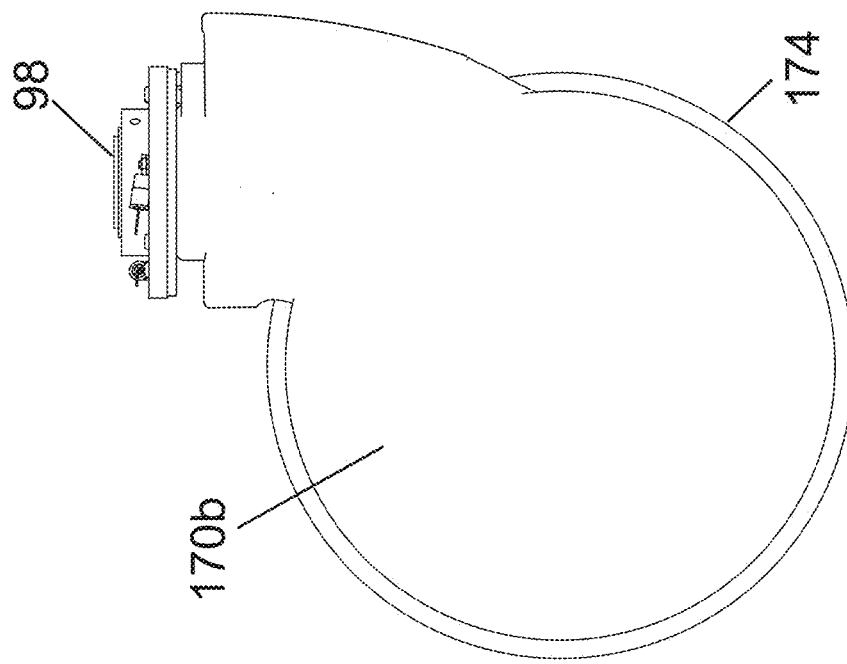
FIG. 6 is a side view of the active component of FIG. 5.
Figure 6A:
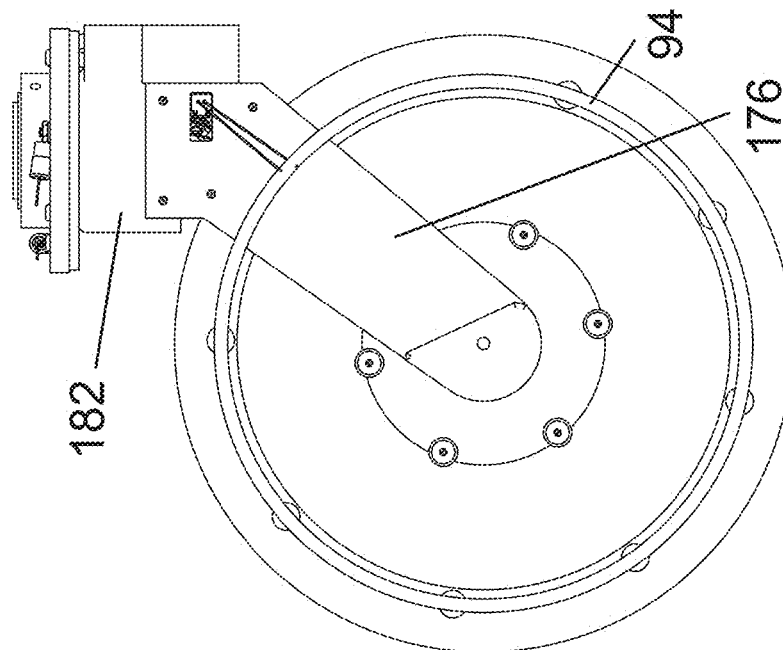
FIG. 6A is similar view to FIG. 6 with the wheel cover removed.
Figure 5A:
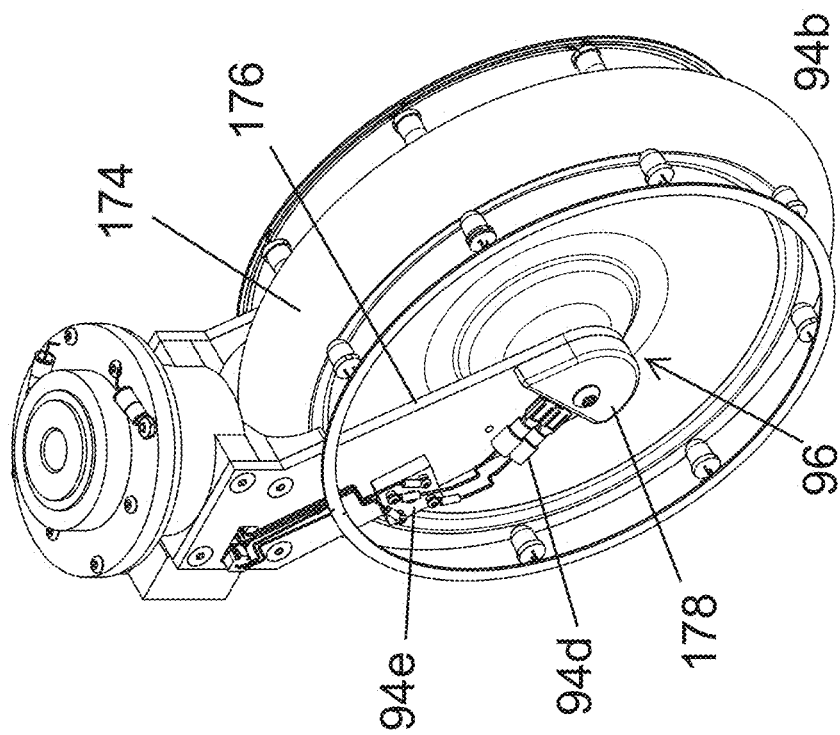
FIG. 5A is similar view to FIG. 5 with the wheel cover removed.
Figure 6C:
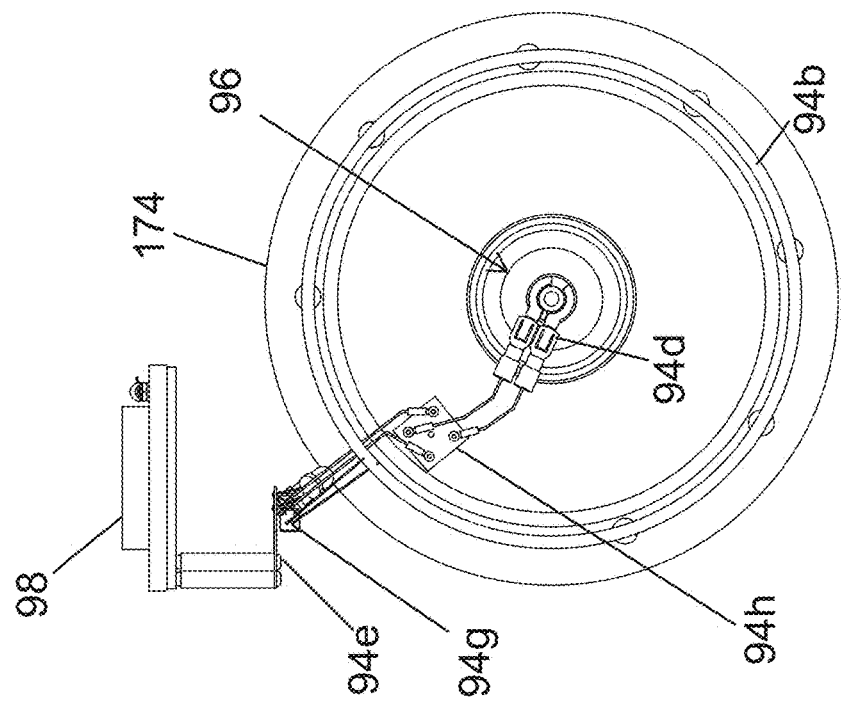
FIG. 6C is similar view to FIG. 6 with the bracket and part of the swivel connection removed.
Figure 6B:
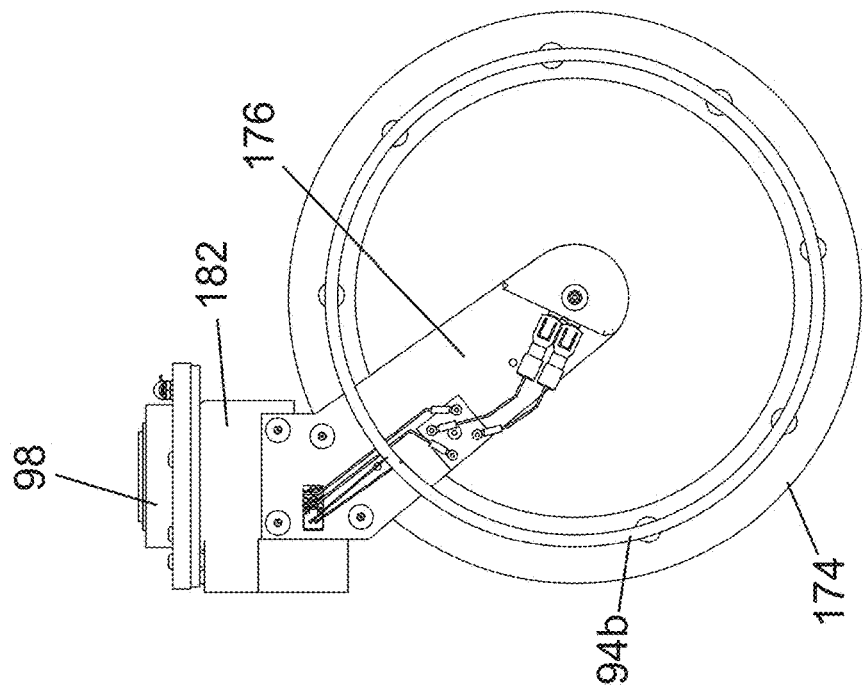
FIG. 6B is the opposed side view of the wheel of FIG. 6A.
Figure 9:
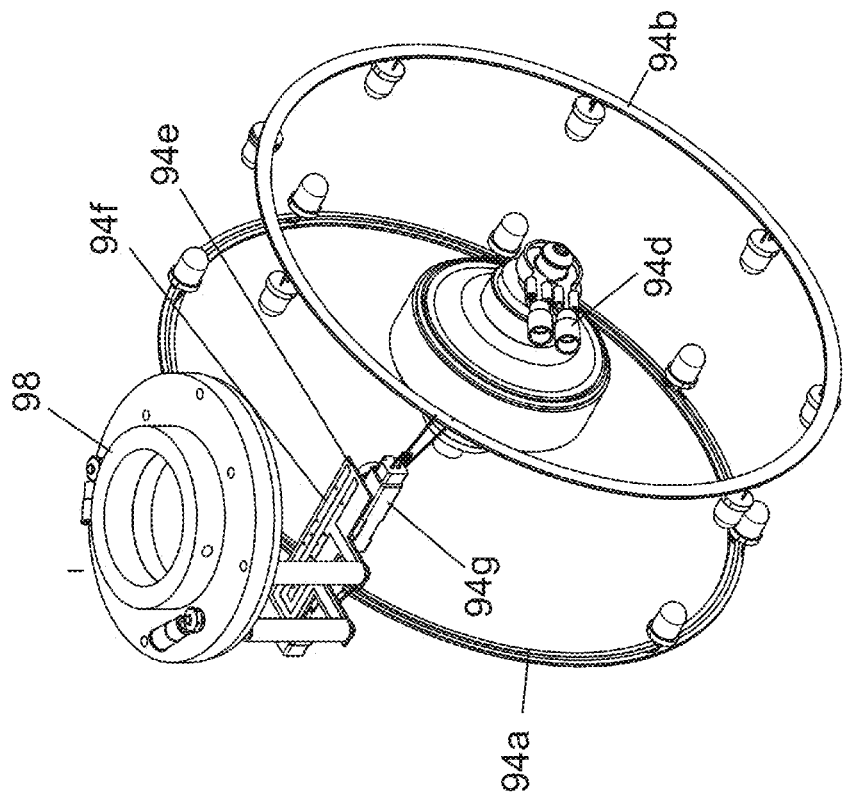
FIG. 9 is another perspective view of the active component of FIG. 5.
Figure 10:
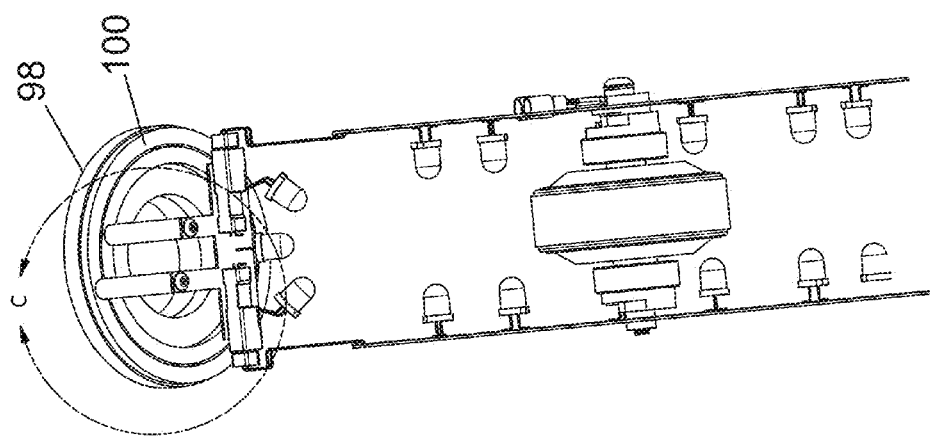
FIG. 10 is a front elevation view of the active component of FIG. 9.

In addition to surfaces that are likely contacted or touched by the patient, caregiver, or worker, other surfaces on the patient support may also be cleaned. For example, the bed's castor wheel assemblies (70) may incorporate a passive or active antimicrobial component. Referring to FIG. 4, castor wheel assembly 70 optionally includes a UV light generator 72, such as a UV LED (or UV LEDs), which washes the wheel 74 of castor wheel assembly 70 with UV light, similar to that described in copending application entitled CLEANING SYSTEM AND EQUIPMENT THEREFOR, filed Nov. 10, 2011, Ser. No. 61/558,190, which is hereby incorporated by reference herein in its entirety. To protect the patient, caregivers or visitors, wheel 74 is covered by shrouds 70a, 70b, which are mounted about wheel 74 and to, for example, the wheel bracket.

In addition or alternatively, wheel 74 may include antimicrobial material, such as antimicrobial bodies incorporated therein, such as by molding, so that when wheel 74 is rolled across a floor, the bacteria that may be picked up from the floor will be killed by the antimicrobial material contained within the wheel itself. When combined with the active antimicrobial properties of the UV light, it is believed that a significantly lower bacteria load on the castor wheel assemblies can be achieved.

For example, the wheel may be formed with a base material and the material with antimicrobial properties (antimicrobial material) dispersed through at least an outer layer of the base material. Further, the base material is selected so that that overtime with normal use it wears down so that more of the antimicrobial material dispersed beneath the outermost surface of the base material is then exposed to the ambient atmosphere to refresh the antimicrobial characteristic of the wheel, in a similar manner as described above in reference to the handholds.

The UV light 72 may be powered by the bed-based network power supply or a power supply onboard the castor wheel assembly. Referring again to FIG. 4, wheel assembly 70 may incorporate a generator 76 that is driven by a gear 78 mounted to the shaft 80 of wheel 74, which powers UV light 72. In addition, generator 76 may be coupled to the bed-based control board for powering other components on the bed. For example, electronic devices with low power requirements could be powered by generator 76. One suitable system includes the bed exit system sold under the trademark CHAPERONE®, by Stryker Corporation of Kalamazoo, Mich.

Alternately, wheel assembly 70 may incorporate therein a stator and a coil. For example the stator may be mounted to the wheel shaft and the coil mounted to the wheel support bracket (not shown) about which the wheel shaft rotates so that the rotating motion of the wheel will induce the current flow through the coil (or vice versa). The coil is then coupled to an optional AC to DC converter and an energy controller, such as a microcontroller to control the electric flow to the UV lights (and other electronic base components to be driven by the wheel based energy supply).

Referring to FIGS. 5-11, the numeral 90 generally designates another embodiment of an active antimicrobial component for generating energy in the form of light, namely UV light, to wash a component of medical apparatus 10 with light. In the illustrated embodiment, active antimicrobial component 90 is configured to wash a wheel of a caster assembly with UV light, including optionally UV-C light.

As best seen in FIGS. 5-9, active antimicrobial component 90 includes a plurality of light sources 92a, such as UV LEDs, which are configured to face the wheel 174 to direct the UV light onto the opposed sides of the wheel. In the illustrated embodiment, lights 92a are mounted to two circuit boards 94a, 94b, such as annular circuit boards, each with a conductive trace 94c, such as a copper trace. Circuit boards 94a, 94b are mounted, for example to the wheel mounting bracket 176 inside the shroud or cover (170a, 170b) of the caster wheel assembly, and coupled to a local power supply, such as a dynamo 96 (via electrical connectors 94d), which generates electricity from the rotation of the wheel. For example, in the illustrated embodiment, dynamo 96 comprises a hub dynamo that is mounted at the hub of the wheel about the wheel's axle 178, which also supported by brackets 176 by bearing assemblies 180. A suitable dynamo is available from Wilfried Schmidt Maschinenbau of Germany. Though it should be understood that a side mounted dynamo may be used as alternative.

In a similar manner as described in reference to wheel 74, wheels 174 may include antimicrobial material, such as antimicrobial bodies incorporated therein, such as by molding, so that when wheel 174 is rolled across a floor, the bacteria that may be picked up from the floor will be killed by the antimicrobial material contained within the wheel itself. Again, the the wheel may be formed with a base material and the antimicrobial material dispersed through at least an outer layer of the base material, with the base material being selected so that that overtime with normal use it wears down so that more of the antimicrobial material dispersed beneath the outermost surface of the base material is then exposed to the ambient atmosphere to refresh the antimicrobial characteristic of the wheel, in a similar manner as described above in reference to the handholds.

Optionally, active antimicrobial component 90 may include a second plurality of light sources 92b, optionally UV LEDs, including UVC LEDs. Lights 92b may be mounted to a transverse circuit board 94e, which has a conductive trace 94f, such as copper trace (best seen in FIG. 9), and which is mounted to collar 182 for rotation with collar 182 relative to wheel assembly mount 98 (which together for a swivel connection for the wheel). Circuit board 94e supports lights 92b so that they straddle the width of the wheel and direct light downwardly across the width or tread of the wheel. Transverse circuit board 94e is electrically coupled to circuit boards 94a, 94b via electrical connectors 94g so that lights can be similarly powered by dynamo 96 through boards 94a and 94b.

Figures 11, 12:
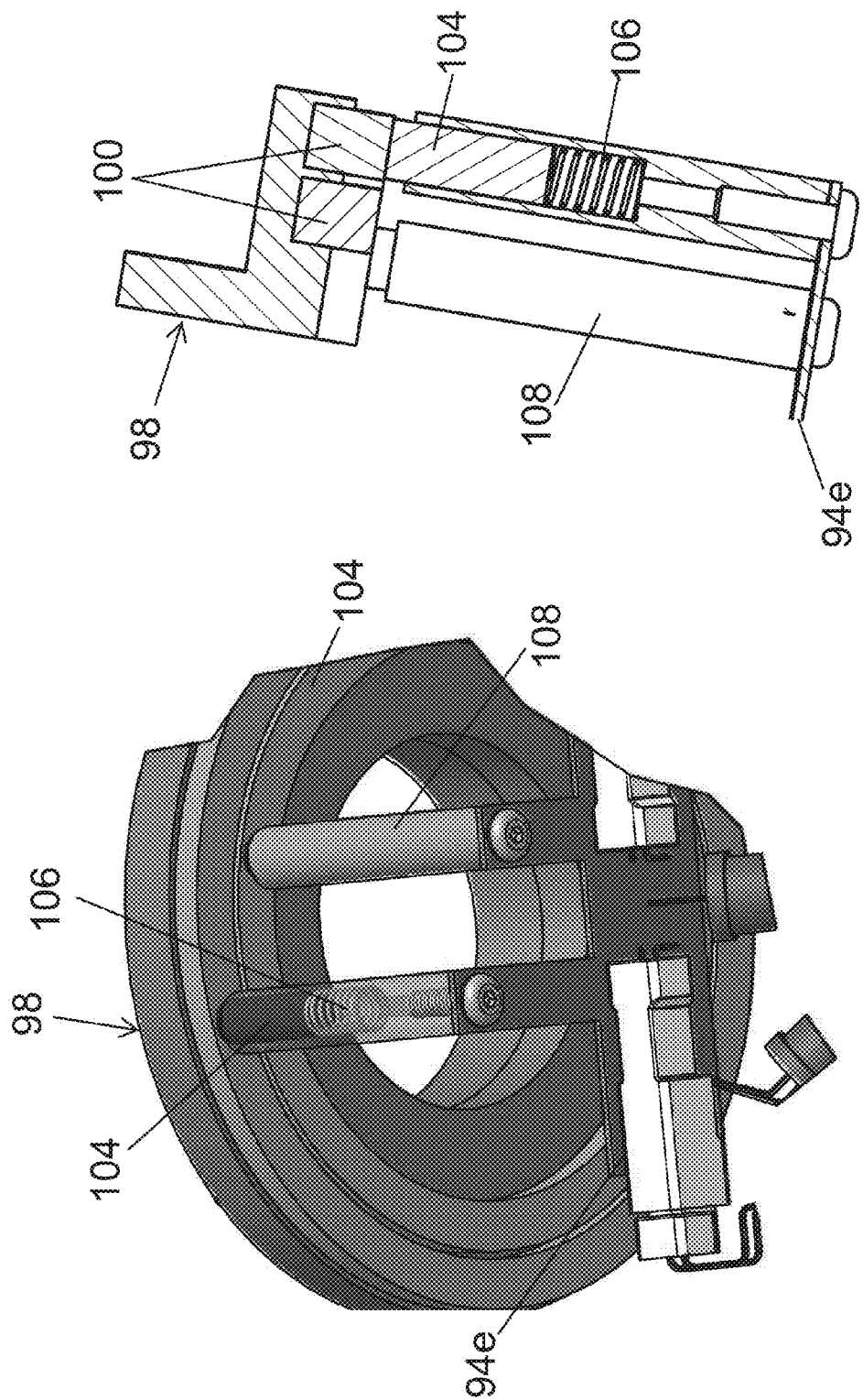
FIG. 11 is an enlarged fragmentary view of swivel mount and circuit board mount of the castor wheel assembly of FIG. 5.
FIG. 12 is cross-section taken through FIG. 11.

Additionally or alternatively, lights 92a and 92b may be powered from the medical apparatus power supply. For example, the swivel connection (98 and 182) of the caster wheel assembly may include a slip ring formed by a pair of annular traces 100, such as copper traces, which are electrically coupled to the medical apparatus power supply, which are then electrically coupled to boards 94a, 94b, and 94e via a dynamic connection 102. In the illustrated embodiment and as best seen in FIGS. 11 and 12, dynamic connection 102 includes electrical brushes 104 that are coupled to board 94e and urged into contact with traces 104 by a pair of springs 106. Springs 106 and brushes 104 may be housed in posts 108, which mount board 94e to collar 182. Alternately to the described brush-based slip ring, a wetted slip ring (that uses no brushes) available for example from Mercotac, or a fiber optic rotary joint, maybe used.

Figure 13:
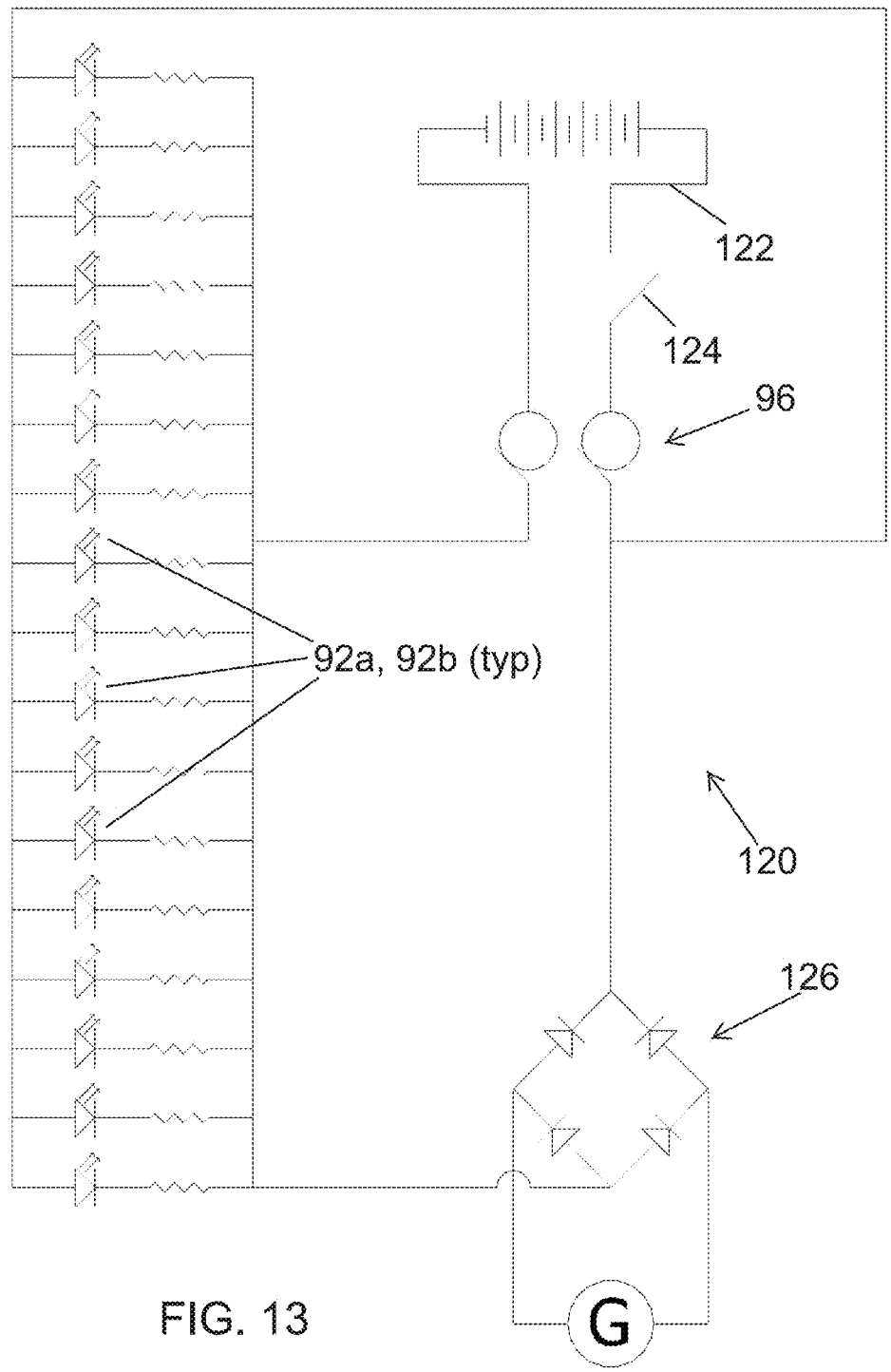
FIG. 13 is schematic drawing of the circuit for the active component in FIGS. 5-12.

In this manner, lights 92a and 92b may be powered either by the medical apparatus power supply or a local power supply (e.g. the dynamo) or both. Alternately, the local power supply may comprise an inductive based power supply, with a transmitting coil electrically coupled to the medical apparatus power supply, and the receiving coil electrically coupled to the circuit boards.

Where the lights are powered by alternate power supplies, the circuitry may incorporate a device to discharge excess current so that, for example, current will not be discharged through the windings of the dynamo. For example, referring to FIG. 13, active antimicrobial component 90 includes a drive circuit 120, which electrically couples dynamo 96 to lights 92a, 92b and also to the equipment based power supply, such one or more batteries 122. Optionally, circuit 120 may incorporate a switch 124 to electrically decouple battery (batteries) 122 from the circuitry and also may incorporate a rectifier 126 in the form of a diode, for example, a Zener diode bridge, that regulates the AC power generated by the dynamo and also prevents discharge through the dynamo coil, for example, when the lights are electrically coupled to both the battery and the dynamo, and both are supplying electricity.

In yet another embodiment, the medical equipment of the present invention may also include structural components in a medical or hospital setting, such as floor panels (e.g. tiles) or wall panels or headers. In each case, copper or copper alloy bodies may be applied to the components or incorporated therein as described in reference to the handholds. In addition to the passive components, active components may also be used to wash the floor or wall panels or header with energy, such as UV light, an electric charge, magnetic field, ultrasound waves, or heat.

Accordingly, the present invention provides components and/or a system of components that automatically clean surfaces on medical equipment, which can provide enhanced infection control. The combination of the two types of components that deliver very different antimicrobial approaches are believe to provide a synergistic effect and ward off or avoid resistance that may exist in bacteria to some treatments. Further, because of the automatic and self-cleaning nature of the present invention, the present invention overcomes many of the physical impediments to manual cleaning.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular. Further, it should be understood that any directional terms used herein, such as "inner," "inwardly," "outer" and "outwardly," are used to assist in describing the invention based on the orientation of the embodiments shown in the illustrations. The use of directional terms should not be interpreted to limit the invention to any specific orientation(s).

The embodiments of the invention in which an exclusive property or privilege is claimed are defined as follows:

1. A patient support comprising:
a patient support surface;
a barrier adjacent said patient support surface;
said barrier or said patient support surface including a body forming an exterior surface of said patient support;
a material having antimicrobial properties embedded in, applied to, or suspended in said body to provide antimicrobial treatment at said exterior surface; and
an energy generation system directing energy to said body to provide an antimicrobial treatment to said body at said exterior surface, said energy generation system operable to generate UV light, wherein the UV light is directed into said body, and said body being formed from a material enabling total internal reflection of the UV light so that the light when directed into said body is substantially retained within said body to thereby protect a patient supported on the patient support from the UV light.

2. A component of medical equipment, said component comprising:
a body, said body being adapted to mount to a patient support and to form an exterior surface of the patient support when mounted to the patient support;
a material having antimicrobial properties embedded in, applied to, or suspended in said body to provide antimicrobial treatment at said exterior surface; and
an energy generation system applying energy to said body to provide an antimicrobial treatment to said body at said exterior surface to thereby protect a patient supported nearby from the energy.

3. The component according to claim 2, in combination with a patient support, said patient support comprising:
a patient support surface;
a barrier adjacent said patient support surface;
said barrier or said patient support surface including said body; and
said energy generation system applying a current, a field, heat, sound waves, or light to provide antimicrobial treatment to said body.

4. The component according to claim 3, wherein said material comprises copper or a copper alloy.

5. The component according to claim 3, wherein said material comprises copper powder or copper alloy powder.

6. The component according to claim 3, wherein said material comprises a copper or copper alloy coating.

7. The component according to claim 3, wherein said material comprises copper bodies suspended in said body.

8. The component according to claim 3, wherein said material comprises a copper plate.

9. The component according to claim 3, wherein said energy generation system generates UV light.

10. A method of cleaning medical equipment comprising:
providing a patient support according to claim 3; and
directing energy into or through the body of the patient support with the energy generation system to thereby provide antimicrobial treatment at said exterior surface.

11. The method according to claim 10, wherein said directing energy includes directing light into the body.

12. The method according to claim 11, wherein said directing light comprises directing UV light into the body at an angle such that there is total internal reflection in the body thereby protecting a patient supported on the patient support from the UV light.

13. The component according to claim 2, wherein said energy generation system generates infrared light.

14. The component according to claim 2, wherein said energy generation system generates current in the range of 1 milliamp to 10 milliamps.

15. The component according to claim 2, wherein said energy generation system generates an electric charge.

16. The component according to claim 2, wherein said energy generation system generates a magnetic field.

17. The component according to claim 2, wherein said energy generation system generates heat.

18. The component of medical equipment according to claim 2, wherein said material comprises at least copper or a copper alloy.

19. The component of medical equipment according to claim 2, wherein said energy generation system generates UV light.

20. The component of medical equipment according to claim 19, wherein the body is formed from a material enabling total internal reflection of the UV light so that the UV light when directed into the body is substantially retained within said body to thereby protect a patient supported on the patient support from the UV light.

21. The component according to claim 2, wherein said body is adapted to form a part of the patient support.

22. The component according to claim 21, wherein said component comprises a side rail, a caster wheel assembly, a headboard, a foot board, or a work surface.

23. The component according to claim 21, wherein said material having antimicrobial properties is suspended in said body.

24. The component according to claim 22, wherein said component comprises a caster wheel assembly, said body forming a wheel of said caster wheel assembly, and said energy generation system generating UV light and directing the UV light to the wheel.

* * * * *